United States Patent [19]

Beste

[11] Patent Number: 4,898,726

[45] Date of Patent: Feb. 6, 1990

[54] INITIATED HAIR STRAIGHTENING COMPOSITION AND SYSTEM

[75] Inventor: Marion D. Beste, Arlington Heights, Ill.

[73] Assignee: Johnson Products Co., Inc., Chicago, Ill.

[21] Appl. No.: 236,054

[22] Filed: Aug. 24, 1988

[51] Int. Cl.$^4$ .......................... A61K 7/09; A45D 7/04
[52] U.S. Cl. ........................................ 424/72; 424/71; 132/204
[58] Field of Search ...................... 424/72, 71; 132/204

[56] References Cited

U.S. PATENT DOCUMENTS

| | | | |
|---|---|---|---|
| 2,405,166 | 8/1946 | Reed et al. | 132/204 |
| 2,464,280 | 3/1945 | Reed et al. | 424/72 |
| 2,464,281 | 3/1945 | Peterson | 424/72 |
| 2,564,722 | 6/1945 | Reed et al. | 132/204 |
| 2,719,814 | 10/1955 | Haefele | 424/71 |
| 3,066,077 | 11/1962 | DeMytt et al. | 424/72 |
| 3,654,936 | 4/1972 | Wajaroff | 132/204 |
| 3,971,391 | 7/1976 | Bore et al. | 424/71 X |

OTHER PUBLICATIONS

Finkelstein et al., "Preparation and Hair Waving Properties of 2,5-Dimercaptoadipic Acid", *J. Soc. Cosm. Chem.*, 13, 253–262 (1962).
Elliott, "Use of a Laboratory Model to Evaluate the Factors Influencing the Performance of Depilatories," *J. Soc. Cosm. Chem.*, 25, 367–377 (p. 74).
Shansky, "New Cold Permanent Waving System," *S.C.C.S.*, 51 32, 34, 37, 65–66 (1976).

Primary Examiner—Ellis P. Robinson
Assistant Examiner—Susan S. Rucker
Attorney, Agent, or Firm—Olson & Hierl

[57] ABSTRACT

A no-base type, aqueous alkali-based hair-straightening composition having a pH between 12 and about 14 initiates and enhances the permanent hair-straightening effect. The hair-straightening composition comprises, as an active hair-straightening agent, a strong alkali, and a water-soluble hair-straightening initiating agent. The initiating agent is a mercapto ($C_4$–$C_6$) dicarboxylic acid having a sulfhydryl functional group on a carbon atom alpha to one or both of the carboxy acid groups, salt thereof or derivative thereof, and is a hair keratin-disulfide reducing agent. The initiated composition particularly augments and enhances the permanent hair-straightening benefits of sodium hydroxide, yet substantially overcomes negative hair conditioning problems normally associated therewith. Thiomalic acid and 2,5-dimercaptoadipic acid are preferred initiating agents. Also disclosed is a hair-straightening system and method for straightening hair with the foregoing compositions.

42 Claims, No Drawings

INITIATED HAIR STRAIGHTENING COMPOSITION AND SYSTEM

TECHNICAL FIELD

This invention relates to alkali-based straightening or relaxing of hair, and in particular to sodium hydroxide-based hair straightening compositions having improved hair-straightening benefits.

BACKGROUND ART

Hair straightening or relaxing has become increasingly popular in view of hair styles which require relatively or perfectly straight hair. Several types of chemical hair straightening products are available. But strong alkali, especially sodium hydroxide, is generally considered the most effective agent for substantially permanently straightening kinky-curly negroid hair.

In order to achieve maximal straightening, however, relatively high concentrations of greater than about 2 weight percent sodium hydroxide are generally applied to and maintained in contact with the hair for a relatively long time. This process results in decreased hair condition benefits and increased skin irritation.

Hair straightening or relaxer products most commonly used in salons and in the home contain as the sole active hair-straightening agent either a strong alkali, such as sodium hydroxide or guanidine hydroxide; a sulfite, typically an ammoniacal mixture of bisulfite and sulfite; or a thiol compound, typically ammonium thioglycolate. All of these types of products exert their primary reducing effect by breaking the cystine disulfide bonds present in hair keratin, referred to as hair keratin-disulfide bonds. The chemical action of alkali-based straightening, sulfite-based straightening and thiol-based straightening is known to differ to varying extents. Alkali, in particular, produces additional stable crosslinks in the hair that are not normally present in virgin hair.

The majority of hair-straightening kits sold for home use are based on the sulfite or thioglycolate straighteners. However, these have several inherent disadvantages. One major disadvantage is the highly offensive odor of the thioglycolate solutions and of the thiol-reduced hair. Another disadvantage is that thiol-based straightening requires the use of an oxidizing neutralizer, such as hydrogen peroxide, to chemically relink the hair keratin-disulfide bonds and to stop the straightening process quickly. Since the thiol-reduced hair is in an alkaline state, any excess neutralizer must also be removed to avoid bleaching the natural color of the hair.

Sulfite-based straighteners have similar disadvantages. For example, sulfite-containing solutions can deteriorate gradually and release offensive odors of sulfur dioxide. Sulfite-reduced hair also must be neutralized by bringing the hair to an alkaline pH to reverse the keratin-sulfite reaction and to chemically re-link the hair keratin-disulfide bonds.

On the other hand, strong alkalis, such as sodium hydroxide and guanidine hydroxide, have several advantages over the sulfite or thioglycolate agents. These alkalis do not have a highly objectionable odor or cause such an odor on reducing the hair. Alkali-straightened hair is treated at a highly alkaline pH of between above 12 and about 14. At that alkalinity, alkalis are known to form stable, irreversible crosslinks of lanthionine and lysinoalanine in the reduced hair making a chemical re-linking step unnecessary. Thus, the only step required following an alkali-based straightening process is to remove substantially all excess alkaline solution to avoid and minimize damage to the hair protein or skin. For this purpose, an acidic shampoo is usually used to neutralize residual alkali on and remove it from the hair and scalp. Guanidine hydroxide, unlike sodium hydroxide, is not chemically stable in solution for any practical storage period. Consequently, it must be freshly prepared prior to using (usually within 24 hours). For this reason, guanidine hydroxide-based straighteners are supplied as a two-component package. Thus, despite its causticity, sodium hydroxide-based hair straightening or relaxer kits, which became available around 1958, are still popular and widely used in professional shops. The sodium hydroxide-based relaxer has also continuously gained popularity for home use since its introduction to the retail market in 1971.

The main advantage of a sodium hydroxide straightener is relatively good straightening of naturally kinky-curly negroid hair. Additionally, the straightening effect is more permanent; i.e., less likely to revert to a curly state after shampooing and wearing than is hair straightened with other straighteners.

However, the sodium hydroxide must remain in contact with kinky-curly hair long enough to allow sufficient irreversible crosslinks to form rather than reversible temporary salt bond linkages. Otherwise, only a loosened wavy curl pattern is achieved, an effect sometimes called texturizing, rather than permanent straightening. Thus, in order to permanently straighten relatively resistant coarse hair having a natural kinky or tight curl pattern, a process time of about 20 minutes or longer ordinarily would be required.

The principal disadvantage of sodium hydroxide-based hair straighteners, of course, is their causticity which can adversely affect hair condition, leaving it in a brittle state and harsh to the touch. Consequently, prolonged or unnecessary exposure of hair to strong alkali at above pH 12 can weaken, break and even dissolve the hair. In the interest of avoiding loss of hair integrity, relatively short process times of about 18 minutes or less are typically employed, thereby sacrificing some measure of permanency. Thus, it would be desirable to initiate the formation of permanent linkages in the cortex of the hair to boost permanent straightening effects within such a practical short process.

The concentration of sodium hydroxide used for modern hair-straightening procedures can vary between about 1.5 to about 3.5 weight percent, depending on whether the product is a "base" type or "no-base" type relaxer. The term "base type relaxer" means that the scalp and hair line must be coated with a protective oleaginous base, such as petrolatum, mineral oil and lanolin, before applying the hair relaxer. The term "no-base type relaxer" means that the scalp need not be coated with a protective base. In some cases, where the no-base type hair relaxer incorporates sodium hydroxide in an oleaginous cream base, a protective base frequently need only be applied to the hairline to protect the skin around the forehead, ears and neckline. No-base type relaxer processes, therefore, are preferred.

Some past attempts have been made to use chemical straighteners, other than sodium hydroxide, sulfite and thioglycolates, such as mercapto-substituted compounds and various combinations of chemical treatments and heat. A discussion of these studies can be found in the books by deNavarre, *The Chemistry and Manufacture of Cosmetics,* Second Edition, Vol. IV, Continental Press, Orlando, Fl. (1975) and by Sagarin, *Cosmetics: Science and Technology,* Second Edition, Vol. 2, Wiley-Interscience, New York, NY (1972). The pertinent disclosures of both of these books are incorporated herein by reference. A review of other chemical hair straighteners and waving agents reported in the patent literature also can be found in *Cosmetics & Toiletries,* 94, 61-69 (April 1979) and 100, 23-29 (April 1985), also incorporated herein by reference. These reported attempts have met with varying degrees of success. But, except for possibly guanidine hydroxide, other chemical hair-straightening agents have not achieved any substantial measure of practical or commercial importance in the hair-straightening arts beyond scientific interest.

In the practice of cold-waving, which by analogy extends to the practice of hair-straightening, thiol compounds that are effective in a cold-wave process are generally used only at pH values below about 10. The terms "cold-wave", "cold-waving" and "cold-wave process" are used in the conventional sense to mean that permanent hair waving or hair straightening is achieved at between ambient room temperature and body temperature, usually at about 30 degrees C (about 86 degrees F) without the assistance of externally applied heat.

The terms "hair-straightening", "hair-relaxing" and grammatical variations thereof will be used interchangeably herein to denote the removal of natural curl from naturally tight curly or wavy hair. The term "permanent hair-straightening" denotes the removal of substantially all curliness to a visibly straight configuration, as opposed to "texturizing hair-straightening" which denotes a loosened wave pattern.

Cosmetically useful thiols in cold wave processes typically have a relatively low molecular weight of below about 140, and are monofunctional, alpha- or beta-mercapto substituted, carboxylic acids having from about 2 to about 5 carbon atoms. However, these thiol compounds are generally not useful for straightening hair at a pH above about 11.5. At above about pH 12, for example, alkali metal salts of thioglycolic acid and of thiolactic acid are known to weaken and dissolve (depilate) hair within a process time of less than about 15 minutes.

Thus, the effective keratin-disulfide reducing action of the foregoing thiols normally cannot be safely combined with alkali to initiate and boost the permanent straightening effects of alkali-based hair-straighteners.

In the interest of maintaining cosmetically safe alkali-based hair straightening, it is desirable to use relatively low levels of sodium hydroxide of between about 1.5 to about 2 weight percent. However, it is necessary to maintain a desirable alkalinity of above pH 12, preferably between about pH 12.5 and about pH 13.5, in order to achieve maximal permanent hair straightening. It is known, for example, that sodium hydroxide at below about pH 12 and at a titratable alkalinity of less than about 0.5 weight percent provides substantially no straightening of curly hair.

Additionally, relatively low levels of alkalinity in combination with short contact times can only form reversible salt linkages in the hair. As a consequence, instead of achieving effective permanent hair-straightening, the caustic action tends to be confined to the surface boundary or cuticle of the hair. This disadvantage further causes a harsher hair condition.

In some instances, strong alkali discolors the natural color of the hair. For example, the tone of natural brown hair is reddened and natural white or grey hair is undesirably yellowed and brightness is dulled. Thus, another disadvantage is delustering of the natural sheen of the hair.

Some strides have been made in improving the condition of sodium hydroxide-straightened hair by incorporating conditioners into the alkaline product. See, for example, U.S. Pat. No. 4,175,572, which issued to the present assignee and which is incorporated herein by reference.

There is still a need for boosting the permanent hair-straightening effects obtained with compositions having relatively low concentrations of sodium hydroxide in a no-base type hair-relaxer process to achieve permanent hair straightening effects equivalent to or greater than those obtained from higher alkali amounts presently used. An ideal sodium hydroxide-based hair straightening composition, system and method would initiate keratin disulfide reduction sufficiently to boost the permanent straightening action of strong alkali in achieving the foregoing benefits within a relatively fast processing time, yet provide good hair condition.

SUMMARY OF THE INVENTION

The hair straightening compositions, system and method of this invention provide an improved alkali-based hair straightener containing a relatively weak thiol hair-straightening initiating agent in which many of the above drawbacks are overcome. In addition, the hair-straightening initiating agent is a polar hair keratin-disulfide reducing agent that is a difunctional mercapto dicarboxylic acid having an active sulfhydryl functional group on the carbon atom alpha to one or both of the carboxy acid groups. Thus, good permanent hair-straightening benefits are initiated and achieved and good hair condition is obtained within a relatively short process time.

This invention specifically relates to an improved, initiated, no-base type aqueous alkali hydroxide-based hair-straightening composition (referred to as a hair-straightener for convenience) having a highly alkaline pH of between above 12 and about 14.

The term "alkali-based hair straightening", as used herein, encompasses compositions and systems where a strong inorganic alkali, such as alkali metal hydroxide, alkaline earth metal hydroxide, or a strong organic hydroxide, such as guanidine hydroxide or quaternary ammonium hydroxide, and the like is employed as the primary active hair-straightening agent at a highly alkaline pH. For convenience, the term "strong alkali" will be used to generally denote these alkali-based hair-straightening agents.

The term "initiated" denotes the presence of a relatively weak thiol initiating agent, as defined below, when the hair-straightener is applied to the hair and which initiates permanent straightening. The term "permanent straightening" as described earlier denotes an uncurling of the naturally tight curl pattern of kinky/curly hair to a substantially straight pattern. This pattern, which is substantially retained on subsequent exposure to humidity or washings, is attributed to the formation of stable lanthionine or lysinoalanine crosslinkages in the hair by strong alkali.

The term "relatively weak thiol", as used herein, denotes a thiol that is difunctional in carboxyl group function and substantially is an ineffective waving agent in a cold-wave process. More particularly, the term "initiating agent" denotes a relatively weak thiol compound that is a water-soluble aliphatic mercapto dicarboxylic acid having about 4 to about 6 carbon atoms ($C_4$–$C_6$), having an available sulfhydryl functional group on a carbon atom alpha to one or both of the carboxy acid groups, and a molecular weight of about 150 or greater. The term "ineffective waving agent" denotes a thiol which, while capable of reducing hair keratin-disulfide bonds, imparts substantially little or no permanent change of hair curl pattern in a conventional cold-wave process of a period of about one hour. Typically, such ineffective waving agents diffuse into the hair slowly thereby exerting their chemical action primarily in the cuticle area of the hair, rather than in the cortex where effective reduction is desired.

In particular, the present hair straightener comprises a mixture of strong alkali as the hair-straightening agent and, in lesser amount, a hair-straightening initiating agent. More particularly, the hair-straightening initiating agent can be a water-soluble salt or derivative of a mercapto ($C_4$–$C_6$) dicarboxylic acid having an available sulfhydryl functional group situated on a carbon atom alpha to one or both of the carboxy acid groups, or it can be the acid itself.

Where the acid itself is included, it is understood that the water-soluble salt of the cation present in the strong alkali, for example sodium in sodium hydroxide-based compositions, forms in situ. Alternatively, of course, the desired salt of the acid can be preformed. However, for convenience in describing the hair-straightener compositions of this invention, reference will be made to the acid as the initiating agent, since its water-soluble salt would be ionized in solution during a hair-straightening procedure.

The invention is described in terms of initiated alkali-based hair straighteners in which the preferred strong alkali is sodium hydroxide, but is not necessarily limited thereby. Surprisingly, it has been found that thiomalic acid (TMA) and 2,5-dimercaptoadipic acid (DMA), which are monofunctional and bifunctional, respectively, with regard to the sulfhydryl group are particularly useful initiating agents. These two thiols are particularly preferred because they have relatively good cosmetic acceptability. They are substantially free of sulfurous malodor, relatively non-toxic for human use and are available in relatively stable powder form.

The invention will be described using the foregoing thiols as preferred initiating agents encompassing the principles of this invention and not by way of limiting the invention. The term "initiated hair straightener" denotes an alkali-based hair-straightener composition containing either TMA or DMA, included either as the acid itself or in the form of water-soluble salt or water-soluble derivative thereof, as disclosed below.

In one surprising aspect, the effective permanent hair straightening by sodium hydroxide was initiated by including either TMA or DMA while retaining good hair condition. In another aspect of this invention, an initiated formulation of what is known in the industry as a Mild-strength hair-straightener achieved a level of permanent straightening at a relatively low concentration of sodium hydroxide which approximated or was substantially equivalent to that obtained with the higher amounts of sodium hydroxide normally used in commercial so-called Regular- or Super-strength products. In addition, the enhanced straightening effect was achieved in a practical substantially short process time.

The term "relatively low" refers to sodium hydroxide present as free base at concentrations of between about 1 weight percent to about 2.25 weight percent, based on the total weight of the hair straightener when it is applied to the hair. The amount of sodium hydroxide present as free base corresponds to the "active" amount of sodium hydroxide available for straightening the hair after including the initiating agent, exclusive of the amount of sodium cation, if any, bound to one or both of the carboxylic acid groups of the initiating agent.

Commercially, active sodium hydroxide of up to about 2.5 weight percent, free base may be needed for permanently straightening coarse and tightly curled/kinky hair. This type of hair generally is resistant to straightening. Higher amounts of sodium hydroxide can be used, of course, but are not desirable, because they increase skin irritancy problems and decrease hair condition.

The term "hair condition" encompasses the objectively measurable character of hair, such as tensile strength; the subjectively perceptible character, such as curliness, natural color and its tonal quality, natural luster or sheen, and odor; and tactile properties, such as smoothness, silkiness, softness and other like properties similarly determined by feel. Permanency of straightening can be generally assessed by visually observing the degree to which the straightened hair reverts to its original curly pattern.

A preferred, initiated no-base type hair-straightening composition of this invention includes sodium hydroxide present in free base form at about 1 to about 2.25 weight percent. A water-soluble, hair-straightening initiating agent can be included as the free acid itself, as a salt thereof, either formed in situ or preformed, or as a derivative thereof at about 0.1 to about 2 weight percent based on the total weight of the hair-straightener applied to the hair.

A particularly preferred hair-straightener having a pH of between about 12.5 to about 13.5 comprises a mixture of sodium hydroxide in free base form at about 1.5 to about 2 weight percent and TMA or DMA at about 0.25 to about 1 weight percent, based on the total weight of the hair-straightener applied to the hair.

In an initiated no-base type hair-straightening system of this invention, the hair-straightening initiating agent can be included as an ingredient along with the strong alkali in a single package supplied for use directly as the hair straightener. Preferably, the hair-straightening initiating agent is packaged separately in a substantially dry powder form or in a dispersed liquid form and is admixed with an aqueous composition containing the sodium hydroxide hair-straightening agent prior to use. In that instance, the hair-straightening system comprises at least two packages; the contents of one containing the sodium hydroxide, and the contents of the second containing the auxiliary hair-straightening initiating agent. When the contents of the first package and second package are mixed, an initiated hair-straightener is provided.

An initiated hair-straightener of this invention has several benefits and advantages. A main benefit is that the permanency of the straightening effect normally obtained with relatively low concentrations of sodium hydroxide hair straighteners can be enhanced to a level approximating or equivalent to that obtained with high concentrations without increasing the attendant problems.

Another benefit is that the natural color of the pre-straightened hair is substantially unchanged after straightening by practicing the principles of this invention. Yet another benefit is that the yellowing discoloration problem normally associated with highly alkaline hair straightening on white or grey hair is minimized. Still another benefit is that skin irritation problems normally associated with the relatively high concentration of sodium hydroxide usually required to provide permanent straightening effects that are equivalent to those obtained with compositions of this invention are avoided.

Moreover, by using the hair-straightening initiating agents of this invention, a lower active amount of sodium hydroxide can be used in commercial sodium hydroxide-based hair-straighteners without sacrificing the permanency of the straightening effect, and at the same time gaining improved hair condition.

Still further advantages and benefits will be apparent to those skilled in the art from the description, examples and claims which follow.

DETAILED DESCRIPTION OF THE INVENTION

It has now been found that aqueous no-base type, strong alkali-based hair-straighteners having a pH between 12 and about 14 can be improved by initiating the hair straightening action of strong alkali, especially sodium hydroxide, while improving hair condition. For convenience, this invention will be discussed in connection with sodium hydroxide as the strong alkali, but this is not intended to so limit the invention.

It is recognized that other strong alkali metal hydroxides, besides sodium hydroxide, can effect hair-straightening without the assistance of heat. Exemplary alkali metal hydroxides include potassium hydroxide and lithium hydroxide. It is further recognized that strong alkalis include alkaline earth metal hydroxide; such as calcium hydroxide, magnesium hydroxide; and organic hydroxides, such as guanidine hydroxide and quaternary ammonium hydroxide which also can effect hair straightening in a cold process. However, sodium hydroxide is generally preferred for commercial cosmetic applications.

This improvement particularly enhances the permanent straightening effect obtained with relatively low amounts of sodium hydroxide that would otherwise provide only marginal or mild hair-straightening. The improvement results from the inclusion of relatively low amounts of a hair straightening initiating agent that is a mercapto ($C_4$–$C_6$) dicarboxylic acid, hair keratin-disulfide reducing agent having a sulfhydryl functional group available on a carbon atom alpha to one or both of the carboxy acid groups.

With reference to sodium hydroxide, the term "relatively low amount" refers to an active amount of titratable free base alkalinity of between about 1 to about 2.25 weight percent sodium hydroxide based on the total weight of the hair-straightening composition when it is applied to the hair. Titratable free base alkalinity, therefore, refers to the unbound strong alkali exclusive of alkali bound as a salt of the initiating agent.

In the United States, sodium hydroxide is typically provided at a titratable free base alkalinity of between about 2 to about 2.25 weight percent in hair-straighteners generally classified as "Mild-strength" and "Regular-strength" in commercial practice. These hair-straightening compositions are generally useful for fine textured hair having only a loose to moderately tight curl pattern.

For straightening coarse and very curly/kinky afro or negroid hair, however, Super-strength hair-straightening compositions having a higher amount of sodium hydroxide are required. Some commercial Super-strength hair straightening compositions can have up to about 3.5 weight percent titratable sodium hydroxide or more. However, as the concentration of sodium hydroxide increases so does the potential for problems relating to skin irritation and hair damage from increased causticity.

For practicing the principles of this invention, therefore, sodium hydroxide, in the form of free base can be at between about 1 weight percent to about 2.25 weight percent, preferably between about 1.5 weight percent to about 2 weight percent and more preferably between about 1.7 weight percent to about 1.9 weight percent. Weight percent refers throughout to the weight of a component based on the total weight of the hair-straightener when it is applied to the hair.

With reference to the disclosed hair-straightening initiating agent of this invention, the term "relatively low amount" refers to a concentration of between about 0.1 weight percent to about 2 weight percent, preferably between about 0.25 and about 1 weight percent and more preferably between about 0.5 to about 0.75 weight percent. In practicing this invention, however, the initiating agent is present in a less than molar equivalent amount than that of the strong alkali to provide for excess active strong alkali in the hair-straightening composition as described in more detail below.

Water-soluble thiol initiating agents suitable for practicing the principles of this invention preferably are substantially crystalline aliphatic mercapto dicarboxylic acids having about 4 to about 6 carbon atoms ($C_4$–$C_6$) in the aliphatic chain and an available sulfhydryl functional group situated on a carbon atom alpha to one or both of the carboxy acid groups. Useful thiol dicarboxylic acids can be either (I) monofunctional as to the sulfhydryl group or (II) bifunctional as to the sulfhydryl group.

Exemplary initiating agents include the following compounds, which is not intended to be an extensive listing or to limit the invention thereto.

(a) 2-Mercaptosuccinic acid, commonly called thiomalic acid (TMA), corresponds to Chemical Abstracts Service Registry Number (CAS) 70-49-5. TMA is a crystalline material having a reported formula weight of about 150.15, a substantially low level of sulfidic odor, and a melting point of about 149–157 degrees C (about 300–315 degrees F). TMA in either the d-form, dl-form or l-form can be employed. TMA is also identified and described in abstract No. 9183 of the *Merck Index*, Tenth Edition, published in 1983 by Merck & Co., Inc. (Rahway, NJ) (hereafter "*Merck*").

(b) 2,3-Dimercaptosuccinic acid (meso-form) corresponds to CAS 304-55-2, having a reported formula weight of about 182.21 and a melting point of about 192–193 degrees C (about 377–379 degrees F). This acid is described under the name, dithiotartaric acid, in U.S. Pat. No. 2,719,814 to Haefele, the pertinent disclosures of which are incorporated herein by reference.

(c) 2,5-Dimercaptoadipic acid (DMA), also called meso-alpha, alpha-dimercaptoadipic acid having a formula weight of about 210 is described, according to the supplier, as having a decomposition point of about 191–192 degrees C. (about 375–378 degrees F.).

The foregoing compounds can be employed in the free acid form or alternatively included in neutralized mono- or di-salt form. The salt form can be an alkali metal salt, such as a sodium or potassium salt, or alkaline earth metal salt, such as a calcium or magnesium salt. It is recognized that a mono- or di-salt can also be prepared with cosmetically useful organic $C_1$–$C_4$ amines, such as monoethanolamine, diethanolamine, triethanolamine, monoisopropanolamine, diisopropanolamine, 2-amino-2-methyl-1,3-propanediol and the like. Inorganic salts are generally preferred for inclusion in strong alkali-based hair straighteners. The sodium salt of the initiating agent is particularly preferred for use in a sodium hydroxide based hair straightener and can be formed in situ.

In addition to the acid form itself, ester and amide derivatives may be employed. For example, mono- and di-esters of lower alkyl alcohols containing up to about 4 carbon atoms, such as methyl, ethyl, propyl and butyl, may be employed, as well as alkoxyalkyl alcohols containing as many as about 7 carbon atoms, for example, methoxyethyl, isopropoxypropyl, etc.

Further, mono- and di-amides of the acid may be used, including those made from hydrazine or primary or secondary lower alkylamines containing from 1 to 4 carbon atoms ($C_1$–$C_4$), such as methyl, ethyl, N-propyl, and butyl amines and alkanolamines, such as monoethanolamine, diethanolamine, monoisopropanolamine, diisopropanolamine, etc.

It is understood that mixed compounds of the foregoing mercapto dicarboxylic acid compounds are included in which one carboxy acid group is neutralized to form a salt and the other is esterified or ammonolyzed to an amide or in which one carboxy acid group is esterified and the other is ammonolyzed as long as the mixed compound functions as an initiating agent within the principles of this invention.

The primary consideration is that the form of the initiating agent used be water-soluble, substantially free of objectionable sulfidic odor, and be relatively stable to aerial oxidation during shelf storage. Another major consideration is that the initiating agent be cosmetically acceptable for use by humans by being substantially non-toxic and non-sensitizing under the highly alkaline hair straightening conditions as practiced herein. To avoid stability problems, a powder form of the initiating agent is preferred, packaged separately for addition to an alkalibased emulsion cream just before use.

Particularly preferred are TMA and DMA, and the invention will be described with these two initiating agents. For convenience, reference to TMA and to DMA initiating agents includes their individual mono- or disalts, whether the salt is formed in situ by the neutralization of the acid form with the strong alkali of a hair straightener or whether the salt is preformed and then included.

TMA and TMA compounds are generally considered weak thiols and ineffective waving agents in a cold-wave process. They are considerably slower acting on the hair than is thioglycolic acid or salts of thioglycolic acid. Where TMA is used as the primary hair keratin-disulfide reducing agent in a cold wave process, a booster additive such as an auxiliary thiol-compound or sulfite compound or a hair-swelling agent, such as urea, is normally required to assist in speeding the reductive action of TMA. Even at alkaline conditions of about pH 11 to about 12.1, TMA has been judged a slow acting depilating agent. See, for example, Elliot, "Use of a Laboratory Model to Evaluate the Factors Influencing the Performance of Depilatories," *J. Soc. Cosm. Chem.*, 25, 3676 (1974), (Elliot), the pertinent disclosures of which are incorporated herein by reference.

DMA, likewise, is a known weak thiol with regard to its hair waving behavior, especially on intact virgin hair, when compared to thioglycolates. Thus, DMA in past studies, generally required added thiol to boost its hair waving activity. A description of DMA and its waving characteristics can be found in Finkelstein et al., "Preparation and Hair Waving Properties of 2,5-Dimercaptoadipic acid," *J. Soc. Cosm. Chem.*, 13, 253 (1962), and in U.S. Pat. No. 3,066,077 issued to DeMytt et al., the disclosures of each being incorporated herein by reference.

Surprisingly, the inclusion of relatively low levels of between about 0.1 to about 2 weight percent TMA or DMA initiating agent based on the total weight of the hair straightener when it is applied to the hair initiates the permanent hair-straightening effect of strong alkali. Preferably, an amount of between about 0.25 to about 1 weight percent, more preferably between about 0.5 and 0.75 weight percent initiating agent is employed.

When TMA or DMA initiating agent was included in a sodium hydroxide-based hair straightener, it was found preferable that sodium hydroxide be present as free base at between about 1 to about 2.25 weight percent, more preferably at about 1.5 to about 2 weight percent and even more preferably at between 1.7 to about 1.9 weight percent.

TMA or DMA can be added in powder form as the acid itself directly into an emulsion cream base containing the sodium hydroxide. Such emulsion cream bases are generally known and supplied in the hair-straightening art. For this purpose, the TMA or DMA also can be included as an ingredient of the cream base. However, at least a two-component system is preferred in which the initiating agent is maintained in dry powder form in one package with the cream base portion containing the sodium hydroxide or other strong alkali in a second package. In this system, the initiated hair straightener can be freshly prepared for use. Alternatively, the initiating agent can be prepared in a liquid form as long as appropriate stabilizers are present.

Where TMA or DMA initiating agents are in the acid form, the total amount of strong alkali in the cream base is adjusted upwards to provide for the neutralizing effect of the acid as it forms a salt having the cation of the strong alkali in situ. For example, where an initiated hair straightener having about 2 weight percent sodium hydroxide in free base form and about 0.5 weight percent TMA or DMA is desired, 100 parts by weight of a cream base having about 2.2 weight percent sodium hydroxide is admixed with about 0.5 grams TMA or DMA as the free acid to form the corresponding sodium salt in situ. Conversely, the TMA or DMA can be provided in a mono- or di-sodium salt form, in which case the cream base portion can be prepared with the appropriate amount of sodium hydroxide as free base.

Alternatively, the initiating agent can be provided, in a two package system, as an aqueous suspension or solution appropriately stabilized against aerial oxidation. Similarly, the initiating agent can be included as an ingredient of the cream base and used directly as a hair straightener as long as the thiol initiating agent is also appropriately stabilized against premature oxidation.

When the initiating agent is present in a sodium hydroxide-based hair-straightener composition, the permanent straightening action of the alkali is enhanced, based on tensile fiber properties as described below. The mechanism by which the initiating agent enhances permanent hair-straightening is not fully understood. Without being bound by any theory, it is believed that the thiol initiating agent effects a reduction of the hair keratin-disulfide within the cuticle surface area of the hair and thereby initiates cortical action by the sodium hydroxide sooner to enhance the formation of stable lanthionine and/or lysinoalanine crosslinkages. Moreover, the initiating action of the thiol is believed to confine itself to a relatively mild surface reduction effect, thereby protecting the integrity of the fiber against alkali degradation. Hence, good permanent straightening is achieved with improved hair condition.

Additionally, improved hair condition is also subjectively discernible by improved visual and good tactile properties. In effect, the straightened hair retains its natural pre-straightened color and luster and soft smooth feel. It is well known that alkali-straightened hair normally tends to be discolored and harshened by the hair-straightening procedure.

A practical, preferred hair-straightening composition has a pH of between 12 and about 14, preferably between about pH 12.5 and about 13.5, with a ratio of sodium hydroxide content as free base to initiating agent of between about 4:1 to about 1.5:1. Preferably, the sodium hydroxide is present at between about 1.5 and about 2 weight percent as free base; and TMA or DMA is present at between about 0.1 and about 2 weight percent, preferably between about 0.2 and about 1 weight percent, preferably between about 0.25 and about 0.5 weight percent, of the total hair-straightening composition.

Initiated hair straightener is intended to be applied to the virgin outgrowth of coarse kinky/curly hair. It is recognized that hair which has previously been, straightened, waved or bleached by other means is already vulnerable to undesirable degradation under highly alkaline conditions, so an initiated hair straightener normally would not be needed or applied to hair in such a state.

As a practical matter, it was found that at about 0.25 to about 0.5 weight percent initiating agent, a hair-straightening composition that would generally be considered a Mild-strength alkali-based product was substantially as effective as a corresponding Regular-strength product without initiating agent, based on tensile fiber studies using the intermittent modulus technique described below. However, by comparison the initiated composition showed greater or enhanced straightening over its corresponding uninitiated counterpart within the same process time. This result suggested that more permanent, irreversible crosslinking had formed within the hair fiber.

More surprisingly, after the initiated augmented boost in permanent straightening action, further chemical action was substantially stopped by the water rinsing step. Thus, substantially no post-rinsing chemical action was observed attributable to residual sulfhydryl or thiol compound in the hair, based on tensile fiber properties measured using an intermittent modulus technique described below. In addition, hair condition was improved.

The term "hair condition" as used herein includes the subjective properties of hair such as luster, color, and desirable tactile properties as well as tensile fiber properties reflected as fiber breakage and visibly straighter curl pattern. The term "tensile fiber properties" includes the physical and chemical characteristics of human hair associated with intact fiber integrity that, in turn, contribute to desirable mechanical properties of good hair condition, i.e., easy combability, manageability and "soft, smooth hand feel."

Thus, it is generally recognized that hair condition is a complex concept that depends on a variety of physical attributes that are subjectively evaluated by practitioners.

One important subjectively evaluated attribute is the natural color of the hair and the brightness of its tone. Discoloration or changes in hair color following an alkali-straightening procedure can be undesirable. For example, dark hair, especially dark brown and black hair, can become reddened, faded or dulled. Particularly troublesome is yellowing of natural white (grey) hair. Another important attribute that can be subjectively seen is an undesirable delustering of the natural sheen or luster associated with the previously described discoloration of the natural color of the hair.

Among the benefits of using an improved hair-straightener of this invention are good hair condition with enhanced brightness and sheen, and non-yellowing of white or grey hair. The mechanism of this invention is not fully understood. However, it is believed that the enhanced speed of the process protects and preserves those constituents in hair, other than cystine disulfide, that can be negatively affected or degraded as a function of time of exposure to alkali, and which contribute to color and sheen.

Instrumental techniques were also employed to objectively measure the effect of initiated sodium hydroxide straightening on various tensile properties of the hair, such as strength and breakage.

One of the instrumental techniques employed measures the stress-strain modulus of hair in terms of fiber elongation and axial swelling while it is actually undergoing a chemical straightening procedure. This technique is called the intermittent modulus technique because changes in the strength of the hair under an intermittently applied additional load are measured. For this purpose, a laboratory model of an intermittent modulus device was constructed and employed.

The intermittent modulus device comprises a balance attached to a beam which controls illumination of a photocell and generates a current. Light control for the photocell is electronically regulated and current is measured on a strip chart recorder.

The instrument balance beam is attached to a test hair fiber. The hair fiber is anchored at each end by a vinyl tab and is laterally positioned. For treatment, the fiber is immersed in a cell containing test product to coat the fiber. The lateral position of the fiber is controlled by a micrometer, and controls are provided on the instrument to assure exact fiber alignment. The length of the hair fiber for convenience is preferably of a gauge length of about 1.5 centimeters (about 0.6 inches) but is not so limited. A constant load is placed on the hair fiber and an additional load is applied at intermittent intervals. For example, a constant load of 0.5 to 1 gram can be applied, and an additional load of 0.5 gram can be applied at 30 second or 60 second intervals.

Changes in the length of the fiber cause proportional changes in the position of the recorder pen. Fiber axial swelling is influenced and controlled by applied chemical treatments thus making it possible to assess the treatment in terms of fiber axial swelling. Axial swelling changes are magnified 200 times on the recorder chart, so that a 30-millimeter (1.2 inch) pen excursion is considered equivalent to about a 1 percent change in a fiber of the foregoing length.

Using this technique, therefore, fiber integrity is measured in terms of both fiber strength and fiber elongation. Fiber strength is determined by the height of the vertical pen excursion. For example, the greater the chemical attack, the weaker the fiber will become and this will be reflected by a greater vertical excursion by the pen. Fiber elongation is related to straightening and is reflected by changes in the vertical starting position of the pen on the recorder chart. Thus, shortening of the fiber as it weakens is readily observable. Restoration of fiber integrity is considered a reversal of weakened fiber strength and supercontraction.

The initiation of permanent hair straightening according to this invention as determined by the intermittent modulus technique can be seen by enhanced proportional changes in the pen excursion and pen position which are attributable to increased cortical activity. This increased cortical activity, in turn, suggests that, in the presence of the initiating agent, greater chemical action takes place in the cortex of the hair. The initiating agents, TMA and DMA, are known to normally exert their reducing action to the outer periphery of the hair, namely the cuticle and the area nearest the cuticle. Strong alkali is known to form irreversible stable lanthionine linkages within the cortex of the hair. Thus, any enhanced activity attributable to the action of the strong alkali is considered permanent straightening. Initiation could be seen by comparing the intermittent modulus tracing pattern against that of an "un-initiated" counterpart control. The term "initiation of permanent straightening" as used herein refers to this foregoing described intermittent modulus pattern.

It is also known that alkali metal salts, especially ionizable sodium salts can influence the swelling of hair by exerting a deswelling effect. This deswelling effect is believed to make the initiating action less pronounced. As the content of an initiating agent increases, so does the content of the corresponding salt formed increase. Consequently, as the ratio of free base to initiating agent (in acid form) increases it apparently overwhelms or masks any delay from or deswelling influence from the salt formed in situ owing to the neutralization of the initiating agent. Thus, the initiating agent is preferably present in a lesser amount to the available strong alkali in a hair-straightening composition of this invention.

In the case of sodium hydroxide-based hair straighteners, intermittent modulus patterns show that at about 1.5 weight percent free alkali, a relatively weak straightening effect is seen in the absence of initiating agent. Thus, a ratio of free base to initiating agent of between about 3.5:1 to about 4.5:1, preferably of about 4:1 is preferred when TMA (as free acid) initiating agent is included at about 0.5 weight percent of the total hair straightener in the foregoing composition.

As the ratio of free base to TMA initiating agent is increased to about 6:1, the effect of the free strong alkali tends to overpower the beneficial effects of initiating agent. Conversely, when the ratio of free base to the initiating agent is decreased to between about 2:1 or below, and particularly at about 0.7:1, the neutralizing effect of the thiol initiating agent tends to substantially decrease the effective straightening of 1.5 to about 2 weight percent free base.

When DMA (as free acid) initiating agent is included at about 0.5 weight percent of a sodium hydroxide-based hair-straightening composition, the intermittent modulus patterns also shows good initiation of permanent hair straightening at a free base:DMA ratio of about 4:1. When about 1 weight percent DMA is employed, the initiating effect of the DMA is still observed at a ratio of free base:DMA of about 1.5:1. At a ratio of free base:DMA of about 0.7:1, however, the neutralized DMA also substantially decreases the straightening effect of 1.5 weight percent free base.

The amount of total strong alkali available as free base can be increased to overcome any deswelling influence from the neutralization of the acidic initiating agent. However, relatively low levels of strong alkali, at a free base level of between about 1 and about 2.25 weight percent, preferably at between about 1.5 and about 2 weight percent, are desired to avoid skin irritancy problem and to minimize alkali harshening.

From our experience, calculated values of percent loss in tensile strength of hair that has been straightened with highly alkaline "lye" or "no-lye" type relaxers obtained with the intermittent modulus technique compare favorably with those obtained by commercially available tensile testers, such as the Scott Tensile Tester, GCA/Precision Scientific, Chicago, IL. Also in this regard, a description of the construction of a laboratory model of an analogous device used to study the performance of depilatories can be found in Elliot, discussed earlier.

The beneficial results observed by the intermittent modulus technique were further corroborated by improved tensile fiber properties obtained with a Scott Tensile Tester and by subjective evaluations of hair condition as well as hair-straightening as described in the following examples.

It is well known that at a pH below about 12, the straightening effect of sodium hydroxide is sacrificed. The chemical action on the hair fiber then primarily consists of uptake of sodium ions that form weak salt bond linkages resulting in swelling and weakening of the hair protein substrate. Thus the free base alkalinity of the product is maintained at between pH 12 to about pH 14, preferably at about pH 12.5 to about 13.5 by adjusting the free base accordingly when thiol acid initiating agent is employed. Alternatively, the thiol initiating agent is added as a preformed alkali metal salt or alkaline earth metal salt or the like.

Improved initiated no-base type aqueous sodium hydroxide-based hair-straightening compositions of this invention are preferably prepared as thickened oil-in-water emulsions, and especially as oleaginous creams. Techniques for preparing such emulsions and creams are well known in the art and a number of these products are commercially available.

Thus, an improved initiated sodium hydroxide-based hair-straightener can be prepared as a single product by combining the hair-straightening initiating agent and the sodium hydroxide in one package.

Alternatively, where the long-term storage stability of the hair-straightening initiating agent under highly alkaline conditions of between about pH 12 and about pH 14 is of concern, the hair-straightening initiating agent can be withheld from the composition containing the active free base sodium hydroxide hair-straightening agent and added just prior to use to form the hair-straightener that is applied to the hair. In this case, the hair-straightening system of this invention comprises at least two packages.

In either the one or two package form, the initiating agent can be either incorporated in the form of a free acid or as a pre-neutralized salt. When it is incorporated as a free acid, the free base is adjusted upwardly in the cream base portion of a two package system to provide for the neutralizing effect of the free acid.

A two-package no-base type hair-straightening system has several advantages. The contents of the first package can comprise an aqueous strong alkali composition having a pH between 12 and about 14, preferably between about pH 12.5 and 13.5, containing sodium hydroxide as a main hair-straightening agent. The sodium hydroxide can be present in a sufficient amount to provide between about 1 and about 2.25 weight percent free base based on the total weight of the hair-straightener that is formed by admixing the contents of the first package with the contents of a second package that includes a hair-straightening initiating agent.

The hair-straightening initiating agent comprises a water-soluble hair keratin-disulfide reducing agent that is a mercapto ($C_4$–$C_6$) dicarboxylic acid having an available sulfhydryl functional group situated on a carbon atom alpha to one or both of the polar carboxy acid groups. The hair-straightening initiating agent is present in an amount sufficient to form an initiated hair-straightening composition when the contents of the second package are admixed with the contents of the first package.

Preferably, the hair straightener obtained from a two-package hair-straightening system comprises, based on the total weight of the admixture, sodium hydroxide in the first package at about 1.5 to about 2 weight percent and hair-straightening initiating agent at about 0.1 weight percent to about 1.5 weight percent, more preferably at about 0.25 to about 1 weight percent.

The contents of the second package can be in either a substantially dry powder form or in a liquid form prior to being admixed with the contents of the first package. Thus, one advantage is that a single Mild-strength hair-straightening kit can be manufactured and provided to be augmented to Regular-strength or Super-strength when needed by the addition of the auxiliary hair-straightening agent. In addition, certain cosmetic adjuvants that are known to be alkali-sensitive or alkali-unstable, such as perfume, product colorant, some surfactants, conditioners and the like, can be included as ingredients in the second package, as long as they are chemically compatible with the auxiliary hair-straightening agent.

For example, as illustrated herein the contents of the second package can be TMA or DMA as the free acid or a salt, preferably as a sodium salt, in powder form. Alternatively, the hair-straightening initiating agent can be dispersed or suspended in water and appropriately sealed against aerial oxidation. In this case the contents of the second package are in liquid form. In either case, the second package can contain some of the cosmetic adjuvants of the hair straightener normally present in the cream base portion of the system, if desired.

In the method of this invention, the disclosed improved sodium hydroxide-based hair straightener can be applied to the hair by techniques well known in the art to at least partially and permanently straighten those portions of the hair that have received no prior chemical hair straightening treatment, i.e., substantially virgin outgrowth. It is generally well known that the length of time that the hair is exposed to a highly alkaline straightener or relaxer product varies with the amount of curl in the hair and the strength of the alkaline straightening agent. Further, the degree of permanent straightening owing to formation of stable lanthionine crosslinkages increases with time.

Typically, the length of time during which a straightener remains on the hair is determined by the practitioner, based on the amount of partial or complete removal of natural curl desired. For coarse, tight/kinky hair, about 20 minutes or more is normally desirable for complete permanent straightening. From a practical viewpoint, a process of time of about 18 minutes or less is desired. Substantially all the hair straightener product is then removed from the hair, preferably by rinsing with water. Substantially immediately thereafter, a post-straightening shampoo is usually applied for purposes of cleansing and removing residual hair composition from the hair or scalp. Any of a number of conventional shampoos typically used by practitioners in the hair straightening arts can be employed. Typically, such shampoos are called neutralizing shampoos and have an acidic to neutral pH.

The following Examples illustrate hair straightening compositions and methods of this invention, but are not intended to be limiting.

EXAMPLE 1

This example illustrates the initiation of permanent hair straightening on hair by an improved sodium hydroxide-based composition containing thiomalic acid (TMA) included as the acid itself as the hair straightening initiating agent. The sodium salt of TMA was formed in situ as described below. For convenience, however, initiation will be described with reference to TMA available from the ionized salt during the hair-straightening procedure.

Initiation was determined by the intermittent modulus technique described earlier while the hair was undergoing a straightening procedure as described below.

A series of initiated hair straightening compositions of this invention, identified as A, C, D, F, G and H, were prepared in the following general manner using the amounts shown in the Table below. TMA in free acid, powder form was mixed directly with a sodium hydroxide-based hair-straightener cream having a pH of between about 12.5 to about 13.5. The compositions were substantially odor-free, i.e., having substantially no detectable sulfurous odor, and were homogeneous.

For comparison, un-initiated control cream compositions, identified as B, E, I and J, were employed having the free base content shown in the Table below.

| Composition No. | Approximate Weight Percent | | Approximate Ratio of Free Base:TMA |
|---|---|---|---|
| | NaOH | TMA | |
| A (Note 1) | 1.95 | 0.5 | 3.9:1 |
| B (Note 2) | 1.9 | — | — |
| C (Note 3) | 1.7 | 0.75 | 2.3:1 |
| D (Note 4) | 1.56 | 0.75 | 2:1 |
| E (Note 5) | 1.5 | — | — |
| F (Note 6) | 1.7 | 1.0 | 1.7:1 |
| G (Note 7) | 1.1 | 1.5 | 0.7:1 |
| H (Note 8) | 2.0 | 0.33 | 6.2:1 |
| I (Note 9) | 2.1 | — | — |

| Composition No. | Approximate Weight Percent | | Approximate Ratio of |
|---|---|---|---|
| | NaOH | TMA | Free Base:TMA |
| J (Note 10) | 2.22 | — | — |

Note 1: 0.1 grams of TMA mixed with 20 grams of a commercial Regular-strength hair straightener cream (control composition J) containing about 2.22 weight percent sodium hydroxide having a pH of between about 12.5 and about 13.5.
Note 2: Hair straightener cream comprising substantially the same emulsion components as the commercial cream described in Note 1, except for the amount of sodium hydroxide.
Note 3: 0.15 grams TMA mixed with 20 grams of a commercial Mild-strength hair straightener cream (control composition I) containing about 2.1 weight percent sodium hydroxide having a pH of between about 12.5 and about 13.5.
Note 4: 0.15 grams TMA mixed with 20 grams of cream composition B.
Note 5: Hair straightener cream comprising substantially the same emulsion components as the commercial cream described in Note 1, except for the amount of sodium hydroxide.
Note 6: 0.1 grams TMA mixed with 10 grams of the commercial Regular-strength hair straightener cream described in Note 1.
Note 7: 0.15 grams TMA mixed with 10 grams of composition B.
Note 8: 0.33 grams of TMA mixed with 10 grams of the commercial Regular strength hair straightener cream described in Note 1.
Note 9: Control commercial Mild-strength hair straightener described in Note 3.
Note 10: Control commercial Regular-strength hair straightener described in Note 1.

The initiating effect of the TMA during the hair-straightening procedure was determined by the intermittent modulus technique, using a fiber of natural brown-color intact hair (R. Weintraub, New York, NY) of gauge length about 1.5 centimeters (about 0.6 inches) mounted between vinyl tabs. A sufficient amount of hair-straightener composition was applied to coat the fiber by immersing the fiber in a cell containing the desired composition at a bath:hair ratio of about 100:1. The fiber was immersed for at least about 10 minutes or until the point where maximum elongation of the fiber was recorded. Thereafter, the cell containing the hair-straightener was removed and the straightened hair was rinsed with tap water.

Throughout the hair-straightening procedure, the fiber was under a constant load of 1 gram with an additional intermittent load of 0.5 gram applied at 60-second intervals. The chemical action of the composition on hair keratin was determined by observing changes in hair fiber integrity reflected in strength, elongation and supercontraction of the fiber undergoing the hair-straightening procedure. These changes were recorded on a strip chart recorder (Sargent-Welch Model XLR) having a 10 millivolt sensitivity using a chart speed of 0.2 centimeters (about 0.1 inches) per minute.

For example, as the strength of the fiber weakens and supercontracts during a typical sodium hydroxide-based hair-straightening treatment, the vertical excursion and starting position of the pen on the chart changes sharply and continuously. Thus, changes attributable to initiating and enhancing, as well as stopping of chemical action were determinable by comparing intermittent modulus results against control hair straighteners containing no initiating agent, based on trace patterns of proportional changes in the recorder pen excursion and pen position.

The results obtained from the use of Composition A was compared against the same hair-straightening procedure carried out using counterparts of un-initiated commercial hair-straightening creams (Compositions B and E) and commercial Mild-strength and Regular-strength compositions (Compositions I and J, respectively) containing sodium hydroxide without the initiating agent.

The results showed that the permanent hair-straightening action of the sodium hydroxide-based hair-straightener was initiated by TMA. After Composition A was applied to the hair, a boost in the elongation of the fiber was observed sooner than with Composition B. Normally, from this and our prior experience, this type of increased elongation corresponds to permanent straightening effects in the hair. The boost observed was judged comparable to that achieved with Composition J, indicating that the TMA initiated permanent hair straightening and enhanced the effect of the relatively low Mild-strength sodium hydroxide content in Composition B to that of the Regular-strength of Composition J.

Based on changes in the intermittent modulus pattern related to fiber elongation and swelling, some boost in hair straightening also was seen with initiated Compositions C and D, compared to un-initiated control Composition E. However, these results also suggested some possible salt deswelling influence from the increased 0.75 weight percent TMA, because the initiating effect was less pronounced than that observed at the 0.5 weight percent TMA level seen with Composition A. These results suggested that the initiating agent in the mixture should be present in lesser molar equivalent amount than that of the strong alkali. The excess strong alkali can thereby compensate for any deswelling effects attributable to increased salt formation at increased amounts of TMA.

An initiating effect was also seen with initiated Composition F when compared to the hair straightening effect of un-initiated Composition B. However, the results again suggested some possible deswelling influence from the increased TMA salt occurred, because the initiating effect of the 1 weight percent TMA was less pronounced than that of the 0.5 weight percent TMA level in Composition A. As discussed earlier, this result also suggested an increased free base:TMA could overcome the influence of the increased TMA salt content. The data further showed that excess strong base should be available for straightening and for activating the initiating action of TMA.

The intermittent modulus result with Composition H showed that the initiating effect of the TMA was less pronounced than that of initiated Composition A but more pronounced than that of un-initiated Composition B. The straightening effect, however, was judged less than that of un-initiated Composition I. This suggests that, as the free base:TMA ratio increased, the initiating effect of the TMA tended to be overpowered or masked by the strong alkali.

The hair-straightening action of non-initiating Compositions B and E was considered to be slow, substantially weak straightening, based on changes attributed to elongation of the fibers.

One benefit observed was that the chemical action of the initiated compositions substantially stopped when they were removed by rinsing the fiber with water. While water rinsing is known to effect some straightening of sodium hydroxide straightened hair by reversing supercontraction, experience shows that some post-rinsing supercontraction continues owing to residual alkali in the hair.

In the case of an initiated composition, the observed pattern for both the rinse and post-rinse curve following rinsing removal of the composition remained substantially uniform with substantially no post-rinse change in vertical pen position. This rinse and post-rinse pattern thereby showed that chemical action on the hair had substantially stopped since further changes in supercontraction were no longer evidenced. In addition, this pattern showed that the TMA initiated the action of the sodium hydroxide on the hair without contributing to increased hair damage from residual sulfhydryl in the hair. On the other hand, a less uniform and typically changing pattern was observed in the vertical pen position during the rinsing and post-rinsing stage for Compositions B and C, as expected.

EXAMPLE 2

This example illustrates the benefits in initiating the hair-straightening effect of sodium hydroxide-based hair-straightening compositions with 2,5-dimercaptoadipic acid (DMA) meso-form. The sodium salt of DMA was formed in situ generally following the procedure of Example 1. Reference is made to DMA available from the ionized salt form during the hair-straightening procedure for convenience.

The preparatory procedure of Example 1 was repeated, except that DMA was mixed into hair-straightening cream compositions in the amounts shown in the Table below.

| Composition No. | Approximate Weight Percent | | Approximate Ratio of Free Base:DMA |
|---|---|---|---|
| | NaOH | DMA | |
| K (Note 11) | 1.9 | 0.5 | 3.8:1 |
| L (Note 12) | 1.5 | 1.0 | 1.5:1 |
| M (Note 13) | 1.6 | 1.0 | 1.6:1 |
| N (Note 14) | 1.52 | 2.1 | 0.7:1 |

Note 11: 0.1 gram of DMA mixed with 22 grams of a commercial Regular-strength hair straightener cream described in Note 1, Example 1.
Note 12: 0.21 grams DMA mixed with 20 grams of Composition B of Example 1.
Note 13: 0.107 grams DMA mixed with 10.7 grams of the commercial Mild-strength hair straightener cream described in Note 3, Example 1.
Note 14: 0.21 grams DMA mixed with 10 grams Composition B, Example 1.

The intermittent modulus results obtained were again compared to those obtained with the control uninitiated Compositions B, E, I and J from Example 1.

Composition K containing 0.5 weight percent DMA initiated the action of the sodium hydroxide. Enhanced elongation of the fiber corresponding to straightening was again observed over that observed with Composition B. The extent of change in fiber length with Composition K was substantially similar to that of Compositions I and J in Example 1.

The intermittent modulus results at 1 weight percent DMA showed Compositions L and M initiated good permanent hair straightening. The hair straightening effect was judged greater than that of the un-initiated controls, Compositions B and E of Example 1.

According to the intermittent modulus results, Composition N showed relatively weak straightening. This result again suggested that, to initiate the action of the DMA, a higher ratio of free base to initiating agent was desirable. This trend was in accordance with that seen in Example 1 using TMA as the initiating agent. Additionally, the compositions containing DMA also were substantially free of sulfidic odor and were homogeneous.

Again, the restorative effect of water rinsing and the post-rinse pattern showed that chemical action affecting supercontraction had substantially ceased. The overall strength of the fiber reflected in the pattern of extension of the fiber at the end of the procedure was about equivalent to that observed with TMA in Example 1.

Thus, the results of this intermittent modulus technique suggested that even at 0.5 weight percent, initiating agent so augments the action of sodium hydroxide that the concentration of sodium hydroxide can be desirably and considerably decreased without sacrificing hair-straightening benefits. By lowering the concentration of sodium hydroxide, increased benefits in hair condition are gained.

EXAMPLE 3

This example illustrates that the same beneficial effects obtained with initiating agent in Examples 1 and 2 were not obtained with 0.5 weight percent of a monofunctional mercaptocarboxylic acid having a sulfhydryl group on the carbon atom beta to the carboxy acid group, i.e., 3-mercaptopropionic acid (MPA). MPA corresponds to CAS 107-96-0, and is known to be a relatively strong cold-waving and depilating agent. It has a formula weight of about 106 and a melting point of about 17 to about 19 degrees C (about 32 to about 66 degrees F).

The procedure of Example 1 was followed except that 0.106 grams MPA were mixed with the Mild-strength commercial Composition N of Example 2 to form a composition identified as Composition O. Composition O containing about 1.9 weight percent sodium hydroxide provided a free base:MPA ratio of about 4:1.

The intermittent modulus result showed that the chemical effect on the hair was too aggressive for achieving the beneficial initiating effect desired. Moreover, the unneutralized MPA, itself, had a cosmetically undesirable stench.

The present invention has been described generally and with respect to preferred embodiments. It will be understood that modifications and variations of the disclosed method and compositions may be made without departing from the spirit and scope of the novel concepts of the present invention.

What is claimed is:

1. An initiated, aqueous, no-base type hair-straightening composition having a pH of between 12 and about 14 comprising a mixture of a strong alkali as a hair-straightening agent and a water-soluble initiating agent that is a mercapto dicarboxylic acid hair keratin-disulfide reducing agent selected from the group consisting of aliphatic dicarboxylic acids having about 4 to about 6 carbon atoms and a sulfhydryl functional group on a carbon atom alpha to one or both of the carboxy acid groups, salts thereof and derivatives thereof.

2. The hair-straightening composition of claim 1 wherein the strong alkali is selected from the group consisting of alkali metal hydroxide, alkaline earth metal hydroxide, guanidine hydroxide and quaternary ammonium hydroxide.

3. The hair-straightening composition of claim 1 wherein the strong alkali is present in free base form at about 1 to about 2.25 weight percent, based on the total weight of the composition.

4. The hair-straightening composition of claim 3 wherein the strong alkali is sodium hydroxide.

5. The hair-straightening composition of claim 1 wherein the initiating agent is selected from the group consisting of thiomalic acid; 2,3-dimercaptosuccinic acid; 2,5-dimercaptoadipic acid; mono- and di-salts thereof with a member of the class consisting of alkali metals, alkaline earth metals and organic $C_1$–$C_4$ amines; mono- and di-esters thereof with a member of the class consisting of lower alkyl alcohols and alkoxyalkyl alcohols containing up to 7 carbon atoms; and mono- and di-amides thereof with a member of the class consisting of primary and secondary alkylamines and lower alkanolamines, containing up to 4 carbon atoms.

6. The hair-straightening composition of claim 1 wherein the initiating agent is present at about 0.1 to about 2 weight percent of the total weight of the composition.

7. The hair-straightening composition of claim 6 wherein the strong alkali is present in free base form at about 1 to about 2.25 weight percent, based on the total weight of the composition.

8. The hair-straightening composition of claim 7 wherein the initiating agent is thiomalic acid.

9. The hair-straightening composition of claim 7 wherein the initiating agent is 2,5-dimercaptoadipic acid.

10. The hair-straightening composition of claim 1 wherein sodium hydroxide in free base form comprises about 1.5 to about 2 weight percent and the initiating agent comprises about 0.25 to about 1 weight percent of the total weight of the composition.

11. The hair-straightening composition of claim 10 wherein the initiating agent is thiomalic acid present as a sodium salt.

12. The hair-straightening composition of claim 10 wherein the initiating agent is 2,5-dimercaptoadipic acid present as a sodium salt.

13. In an improved no-base aqueous hair-straightening composition having a pH of between 12 and about 14 containing sodium hydroxide in free base form as the active hair-straightening agent, the improvement comprising initiating permanent hair-straightening by the inclusion of a water-soluble thiol initiating agent that is a water-soluble mercapto ($C_4$–$C_6$) dicarboxylic acid, hair keratin-disulfide reducing agent having a sulfhydryl functional group on a carbon atom alpha to one or both carboxy acid groups, salts thereof and derivatives thereof.

14. The hair-straightening composition of claim 13 wherein the initiating agent is selected from the group consisting of thiomalic acid; 2,3-dimercaptosuccinic acid; 2,5-dimercaptoadipic acid; mono- and di-salts thereof with a member of the class consisting of alkali metals, alkaline earth metals and organic $C_1$–$C_4$ amines; mono- and di-esters thereof with a member of the class consisting of lower alkyl alcohols and alkoxyalkyl alcohols containing up to 7 carbon atoms; and mono- and di-amides thereof with a member of the class consisting of primary and secondary alkylamines and lower alkanolamines, containing up to 4 carbon atoms.

15. The hair-straightening composition of claim 13 wherein sodium hydroxide is present as a free base at about 1 to about 2.25 weight percent of the total weight of the composition.

16. The hair-straightening composition of claim 13 wherein the hair-straightening initiating agent comprises about 0.1 to about 2 weight percent of the total weight of the composition.

17. The hair-straightening composition of claim 15 wherein the hair-straightening initiating agent is thiomalic acid included at about 0.25 to about 1 weight percent of the total weight of the composition.

18. The hair-straightening composition of claim 15 wherein the hair-straightening initiating agent is 2,5-dimercaptoadipic acid included at about 0.25 to about 1 weight percent of the total weight of the composition.

19. The hair-straightening composition of claim 13 wherein the sodium hydroxide in free base form comprises about 1.5 to about 2 weight percent and the initiating agent comprises about 0.25 to about 0.5 weight percent of the total weight of the composition.

20. The hair-straightening composition of claim 19 wherein the initiating agent is thiomalic acid.

21. The hair-straightening composition of claim 19 wherein the initiating agent is 2,5-dimercaptoadipic acid.

22. A no-base type aqueous hair-straightening composition having a pH of between about 12.5 and about 13.5 comprising, as the active hair-straightening agent, about 1.5 to about 2 weight percent sodium hydroxide in free base form and as a hair-straightening initiating agent, about 0.25 to about 0.5 weight percent thiomalic acid based on the total weight of the composition.

23. A no-base type aqueous hair-straightening composition having a pH of between about 12.5 and about 13.5 comprising, as the active hair-straightening agent, about 1.5 to about 2 weight percent sodium hydroxide in free base form and as a hair-straightening initiating agent, about 0.25 to about 1 weight percent 2,5-dimercaptoadipic acid based on the total weight of the composition.

24. An improved initiated no-base type hair-straightening system in at least two packages comprising:
(a) a first package comprising an aqueous composition having a pH between 12 and about 14 containing, as a hair-straightening agent, sodium hydroxide in an amount sufficient to provide sodium hydroxide in free-base form based on the total weight of a hair-straightener to be applied to the hair; and
(b) a second package including a hair-straightening initiating agent comprising a water-soluble hair keratin-disulfide reducing agent selected from the group consisting of aliphatic mercapto dicarboxylic acids having about 4 to about 6 carbon atoms and having a sulfhydryl functional group on a carbon atom alpha to one or both of the carboxy acid groups, salts thereof and derivatives thereof present in an amount sufficient to form the hair-straightener when the contents of the second package are admixed with the contents of the first package, the amount of hair-straightening initiating agent being less than the free base of sodium hydroxide in the admixture.

25. The hair-straightening system of claim 24 wherein the hair-straightening initiating agent comprises about 0.1 to about 2 weight percent based on the total weight of the admixture.

26. The hair-straightening system of claim 24 wherein the initiating agent is present as a sodium salt.

27. The hair-straightening system of claim 24 wherein the initiating agent is selected from the group consisting of thiomalic acid; 2,3-dimercaptosuccinic acid; 2,5-dimercaptoadipic acid; mono- and di-salts thereof with a member of the class consisting of alkali metals, alkaline earth metals and organic amines; mono- and di-esters thereof with a member of the class consisting of lower alkyl alcohols and alkoxyalkyl alcohols containing up to 7 carbon atoms; and mono- and di-amides thereof with a member of the class consisting of primary and secondary alkylamines and lower alkanolamines, containing up to 4 carbon atoms.

28. The hair-straightening system of claim 24 wherein the sodium hydroxide in the first package provides about 1.5 to about 2 weight percent sodium hydroxide in free base form and the hair-straightening initiating agent comprises about 0.25 to about 0.5 weight percent based on the total weight of the hair-straightener.

29. The hair-straightening system of claim 28 wherein the hair-straightening initiating agent is thiomalic acid.

30. The hair-straightening system of claim 24 wherein the sodium hydroxide in the first package provides about 1.5 to about 2 weight percent sodium hydroxide in free base form and the hair-straightening initiating agent comprises about 0.25 to about 1 weight percent based on the total weight of the hair-straightener.

31. The hair-straightening system of claim 30 wherein the initiating agent is 2,5-dimercaptoadipic acid.

32. The hair-straightening system of claim 24 wherein the contents of the first package are in an emulsion cream form before being admixed with the contents of the second package.

33. The hair-straightening system of claim 24 wherein the contents of the second package are in a substantially dry powder form before being admixed with the contents of the first package.

34. The hair-straightening system of claim 24 wherein the contents of the second package further include cosmetic adjuvants.

35. The hair-straightening system of claim 24 wherein the contents of the second package are in an aqueous liquid form before being admixed with the contents of the first package.

36. In a method of straightening hair with a no-base type aqueous hair-straightening composition in which the hair-straightening composition is applied to the hair and the hair is physically smoothed, rinsed, shampooed, set and dried, the improvement which comprises using as the active hair-straightener the composition of claim 1.

37. In a method of straightening hair with a no-base type aqueous hair-straightening composition in which the hair-straightening composition is applied to the hair and the hair is physically smoothed, rinsed, shampooed, set and dried, the improvement which comprises using as the active hair-straightener the composition of claim 13.

38. In a method of straightening hair with a no-base type aqueous hair-straightening composition in which the hair-straightening composition is applied to the hair and the hair is physically smoothed, rinsed, shampooed, set and dried, the improvement which comprises using as the active hair-straightener the composition of claim 22.

39. In a method of straightening hair with a no-base type aqueous hair-straightening composition in which the hair-straightening composition is applied to the hair and the hair is physically smoothed, rinsed, shampooed, set and dried, the improvement which comprises using as the active hair-straightener the composition of claim 23.

40. In a method of straightening hair with a no-base aqueous hair-straightening composition in which the hair-straightening composition is applied to the hair and the is hair physically smoothed, rinsed, shampooed, set and dried, the improvement which comprises using as the active hair-straightener the composition obtained with the hair-straightening system of claim 24.

41. In a method of straightening hair with a no-base aqueous hair-straightening composition in which the hair-straightening composition is applied to the hair and the is hair physically smoothed, rinsed, shampooed, set and dried, the improvement which comprises using as the active hair-straightener the composition obtained with the hair-straightening system of claim 29.

42. In a method of straightening hair with a no-base aqueous hair-straightening composition in which the hair-straightening composition is applied to the hair and the is hair physically smoothed, rinsed, shampooed, set and dried, the improvement which comprises using as the active hair-straightener the composition obtained with the hair-straightening system of claim 30.

* * * * *

UNITED STATES PATENT AND TRADEMARK OFFICE
CERTIFICATE OF CORRECTION

PATENT NO. : 4,898,726

DATED : February 6, 1990

INVENTOR(S) : Marion D. Beste

It is certified that error appears in the above-identified patent and that said Letters Patent is hereby corrected as shown below:

On the title page, under item [19], "Beste" should be --DenBeste--.
On the title page, in item [73]:
The name of the inventor "Marion D. Beste" should
    read --Marion DenBeste--

Signed and Sealed this

Second Day of April, 1991

Attest:

HARRY F. MANBECK, JR.

*Attesting Officer*            *Commissioner of Patents and Trademarks*